(12) United States Patent
Galli et al.

(10) Patent No.: US 7,119,087 B2
(45) Date of Patent: Oct. 10, 2006

(54) 4-(OXAZOLOPYRIDIN-2-YL)-1,4-DIAZABI-CYCLO-[3.2.2]NONANE DERIVATIVES, PREPARATION AND THERAPEUTIC USE THEREOF

(75) Inventors: Frédéric Galli, Vaucresson (FR); Odile Leclerc, Massy (FR); Alistair Lochead, Charenton le Pont (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 10/495,936

(22) PCT Filed: Nov. 20, 2002

(86) PCT No.: PCT/FR02/03978

§ 371 (c)(1),
(2), (4) Date: May 18, 2004

(87) PCT Pub. No.: WO03/044024

PCT Pub. Date: May 30, 2003

(65) Prior Publication Data

US 2005/0004128 A1    Jan. 6, 2005

(30) Foreign Application Priority Data

Nov. 23, 2001  (FR) .................................. 01 15152

(51) Int. Cl.
*A61P 25/00*  (2006.01)
*A61K 31/55*  (2006.01)
*C07D 519/00*  (2006.01)

(52) U.S. Cl. ....................... 514/219; 514/221; 540/556

(58) Field of Classification Search ................ 514/219, 514/221; 540/556

See application file for complete search history.

(56) References Cited

U.S. PATENT DOCUMENTS

| 4,826,848 | A  |    | 5/1989  | Janssens et al. ............ 514/258 |
| 6,407,095 | B1 |    | 6/2002  | Lochead et al. ............ 514/221 |
| 6,809,094 | B1 | *  | 10/2004 | O'Neill et al. .............. 514/221 |
| 2003/0153574 | A1 |  | 8/2003  | Galli et al. ................. 514/249 |

FOREIGN PATENT DOCUMENTS

| EP | 1219622 | 7/2002 |
| WO | WO 00/34279 | 6/2000 |

\* cited by examiner

*Primary Examiner*—Brenda Coleman
(74) *Attorney, Agent, or Firm*—Balaram Gupta

(57) ABSTRACT

Compound corresponding to the general formula (I)

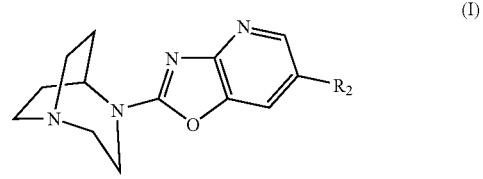

in which $R_2$ represents a chlorine atom, a methyl group or a 3-thienyl group.

Therapeutic application.

9 Claims, No Drawings

4-(OXAZOLOPYRIDIN-2-YL)-1,4-DIAZABI-CYCLO-[3.2.2]NONANE DERIVATIVES, PREPARATION AND THERAPEUTIC USE THEREOF

This application is a National Stage entry under 35 U.S.C. § 371 of International application No. PCT/FR02/03,978, filed Nov. 20, 2002 which is incorporated herein by reference in its entirety.

The present invention relates to compounds that are ligands of the nicotinic receptors, which are useful in the treatment or prevention of disorders associated with dysfunction of the nicotinic receptors, especially in the central nervous system.

The compounds of the present invention correspond to the general formula (I)

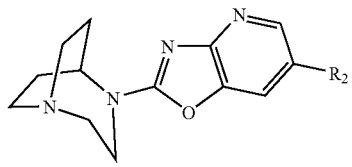

(I)

in which $R_2$ represents a chlorine atom, a methyl group or a 3-thienyl group.

The compounds of the invention may exist in the form of bases or acid-addition salts.

Compounds of general formula (I) are suggested in patent application EP-1 219 622; however, they are not specifically described therein.

In accordance with the invention, the compounds of general formula (I) may be prepared via a process illustrated by the scheme hereinbelow.

1,4-Diazabicyclo[3.2.2]nonane of formula (V) is reacted with a compound of general formula (VI) in which $R_2$ is as defined above, and W represents a halogen atom or a methylsulfanyl group.

The compounds of general formula (VI) are accessible via methods described in the literature, for instance in *J. Org. Chem.* 1995, 60(17), 5721.

The preparation of 1,4-diazabicyclo[3.2.2]-nonane is described in *J. Med. Chem.* 1993, 36, 2311–2320.

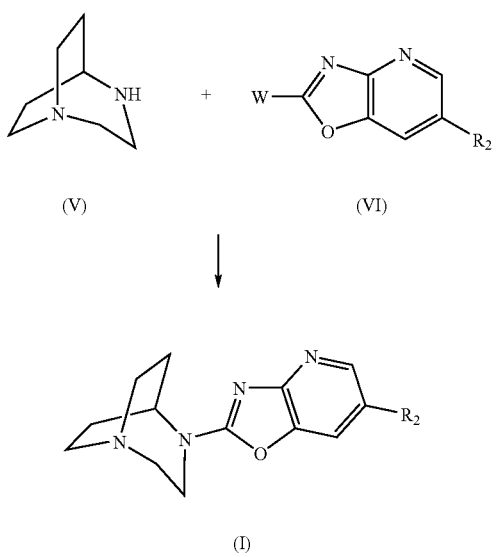

The examples that follow illustrate the preparation of a number of compounds of the invention. The elemental microanalyses and the IR and NMR spectra, and also, in certain cases, the x-ray diffraction spectra, confirm the structures of the compounds obtained.

The numbers indicated in parentheses in the example titles correspond to those in the first column of the table given later.

In the compound names, the hyphen "-" forms part of the word, and the underscore mark "_" serves merely to indicate the line break; it should be deleted if it does not occur at a line break, and should not be replaced either with a normal hyphen or with a space.

EXAMPLE 1 (COMPOUND 1)

4-(6-Thien-3-yloxazolo[4,5-b]pyrid-2-yl)-1,4-diazabicyclo[3.2.2]nonane hydrobromide 1:2

0.2 g (0.62 mmol) of 4-(6-bromooxazolo[4,5-b]pyrid-2-yl)-1,4-diazabicyclo[3.2.2]nonane, 0.079 g (0.62 mmol) of 3-thiopheneboronic acid and 0.024 g of tetrakis(triphenylphosphine)palladium suspended in 10 ml of toluene are successively introduced into a 25 ml reactor. 1 ml of aqueous 2M sodium carbonate solution and 0.1 ml of ethanol are then added and the mixture is refluxed for 12 hours.

The resulting mixture is poured into 10 ml of water, the aqueous phase is extracted with chloroform, the organic phases are dried over magnesium sulfate, filtered and concentrated under reduced pressure, and the residue is purified by chromatography on a silica plate, elating with a 90/10/1 mixture of chloroform, methanol and aqueous anunonia. 0.05 g of product is obtained, which is dissolved in 10 ml of acetone, followed by addition of 0.05 ml of a 33% solution of hydrobromic acid in acetic acid. The crystals are collected by filtration.

0.04 g of product is obtained.

Melting point: 316–319° C.

EXAMPLE 2 (COMPOUND 2)

4-(6-Methyloxazolo[5,4-b]pyrid-2-yl)-1,4-diazabicyclo[3.2.2]nonane hydrobromide 1:2

0.3 g (0.93 mmol) of 4-(6-bromooxazolo[5,4-b]pyrid-2-yl)-1,4-diazabicyclo[3.2.2]nonane, 0.004 g (0.02 mmol) of palladium diacetate and 0.022 g (0.08 mmol) of tris(o-tolyl)phosphine dissolved in 2 ml of dimethylformamide are successively introduced into a 10 ml reactor under argon. 0.18 ml (1.3 mmol) of triethylamine and 0.15 ml (1.11 mmol) of tetramethyltin are added and the mixture is refluxed for 4 hours.

The reaction medium is diluted with ethyl ether and filtered, and the filtrate is concentrated under reduced pressure. The residue is purified by chromatography on a column of silica gel, eluting with a 92/8/0.8 mixture of chloroform, methanol and aqueous ammonia. 0.12 g of product is obtained, which is dissolved in 20 ml of acetone, followed by addition of 024 ml of a 33% solution of hydrobromic acid in acetic acid. The crystals are collected by filtration.

0.12 g of product is obtained.

Melting point: 286–287° C.

The table that follows illustrates the chemical structures and the physical properties of the three compounds of the invention. In the "salt" column, "HBr" denotes a hydrobromide. The acid: base molar ratios are indicated adjacent.

TABLE (I)

| No. | R$_2$ | Salt | m.p.(° C.) |
|---|---|---|---|
| 1 | 3-thienyl | HBr 2:1 | 316–319 |
| 2 | CH$_3$ | HBr 2:1 | 286–287 |
| 3 | Cl | HBr 2:1 | 298–299 |

The compounds of the present invention were studied as regards their affinity with respect to nicotinic receptors containing the $\alpha_4\beta_2$ subunit according to the methods described by Anderson and Arneric, *Eur. J. Pharmacol* (1994), 253, 261, and by Hall et al., *Brain Res.* (1993), 600, 127.

Male Sprague Dawley rats weighing 150 to 200 g are decapitated and the entire brain is removed quickly, homogenized in 15 volumes of 0.32 M sucrose solution at 4° C. and then centrifuged at 1000×g for 10 min. The pellet is discarded and the supernatant is centrifuged at 20 000×g for 20 min at 4° C. The pellet is recovered and homogenized using a Polytron™ mill in 15 volumes of double-distilled water at 4° C., followed by centrifugation at 8000×g for 20 min. The pellet is discarded and the supernatant and the "buffy coat" are centrifuged at 40 000×g for 20 min, the pellet is recovered, resuspended in 15 ml of double-distilled water and centrifuged again at 40 000×g, before being stored at −80° C.

On the day of the experiment, the tissue is thawed slowly and suspended in 3 volumes of buffer. 150 μl of this membrane suspension are incubated at 4° C. for 120 min in the presence of 100 μl of 1 nM [$^3$H]cytisine in a final volume of 500 μl of buffer, in the presence or absence of test compound. The reaction is stopped by filtration on Whatman GF/B™ filters pretreated with polyethyleneimine, the filters are rinsed with 2×5 ml of buffer at 4° C. and the radioactivity retained on the filter is measured by liquid scintigraphy. The non-specific binding is determined in the presence of 10 μM (−)-nicotine; the non-specific binding represents 75 to 85% of the total binding recovered on the filter. For each concentration of test compound, the percentage of inhibition of the specific binding of [$^3$H]cytisine is determined, followed by calculating the IC$_{50}$ value, which is the concentration of compound which inhibits the specific binding by 50%.

The IC$_{50}$ values for the purest compounds of the invention are between 0.6 and 10 μM.

The compounds of the invention were also studied as regards their affinity with respect to nicotinic receptors containing the α7 subunit, according to the methods described by Mark and Collins, *J. Pharmacol. Exp. Ther.* (1982), 22, 564 and Marks et al., *Mol. Pharmacol.* (1986), 30, 427.

Male OFA rats weighing 150 to 200 g are decapitated, the entire brain is removed quickly and homogenized using a Polytron™ mill in 15 volumes of a 0.32 M sucrose solution at 4° C., followed by centrifugation at 1000×g for 10 min. The pellet is discarded and the supernatant is centrifuged at 8000×g for 20 min at 4° C. The pellet is recovered and homogenized using a Polytron™ mill in 15 volumes of double-distilled water at 4° C., followed by centrifugation at 8000×g for 20 min. The pellet is discarded and the supernatant and the buffy coat are centrifuged at 40 000×g for 20 min. The pellet is recovered, resuspended with 15 volumes of double-distilled water at 4° C. and centrifuged again at 40 000×g for 20 min, before storing it at −80° C.

On the day of the experiment, the tissue is thawed slowly and suspended in 5 volumes of buffer. 150 μl of this membrane suspension is preincubated at 37° C. for 30 min, in the dark, in the presence or absence of the test compound. Next, the membranes are incubated for 60 min at 37° C., in the dark, in the presence of 50 μl of 1 nM [$^3$H] α-bungarotoxin in a final volume of 250 μl of 20 mM HEPES buffer. The reaction is stopped by filtration through Whatman GF/C# filters pretreated for 3 hours with 0.05% polyethyleneimine. The filters are rinsed with 2×5 ml of buffer at 4° C. and the radioactivity retained on each filter is measured by liquid scintigraphy. The non-specific binding in the presence of α-bungarotoxin at 1 μM final is determined; the non-specific binding represents about 60% of the total binding recovered on the filter. For each concentration of test compound, the percentage of inhibition of the specific binding of [$^3$H] α-bungarotoxin is determined, followed by calculation of the IC$_{50}$ value, which is the concentration of compound which inhibits the specific binding by 50%.

The IC$_{50}$ values for the purest compounds of the invention are between 0.001 and 0.6 μM.

The preceding results show that the compounds of the invention are selective ligands for the $\alpha_7$ subunits of the nicotinic receptor.

The results of the various tests suggest the use of the compounds in the treatment or prevention of disorders associated with dysfunction of the nicotinic receptors, especially in the central nervous system.

These disorders comprise cognitive impairment, more specifically memory impairment, but also attention impairment, associated with Alzheimer's disease, pathological ageing (Age Associated Memory Impairment, AAMI), Parkinson's disease, trisomy 21 (Down's syndrome), Korsakoff's alcoholic syndrome and vascular dementia (multi-infarct dementia, MID).

The compounds of the invention may also be useful in the treatment of the motor disorders observed in Parkinson's disease or other neurological diseases such as Huntington's chorea, Tourette's syndrome, tardive dyskinesia and hyperkinesia.

The compounds of the invention can also constitute a curative or symptomatic treatment for acute neurodegenerative pathologies such as strokes and cerebral hypoxic episodes, and also chronic neurodegenerative pathologies, for instance Alzheimer's disease. They may also be used in cases of psychiatric pathologies: schizophrenia, depression, anxiety, panic attacks, compulsive and obsessive behavior.

They can prevent the symptoms caused by withdrawal from tobacco, from alcohol and from various substances that induce a dependency, such as cocaine, LSD, cannabis and benzodiazepines.

Consequently, a subject of the present invention is also pharmaceutical compositions containing an effective dose of at least one compound according to the invention, in base form or in the form of a pharmaceutically acceptable salt or solvate, and as a mixture, where appropriate, with suitable excipients.

The said excipients are chosen according to the pharmaceutical form and the desired mode of administration.

The pharmaceutical compositions according to the invention may thus be intended for oral, sublingual, subcutaneous, intramuscular, intravenous, topical, intratracheal, intranasal, transdermal, rectal or intraocular administration.

The unit forms of administration may be, for example, tablets, gel capsules, granules, powders, oral or injectable solutions or suspensions, transdermal patches or suppositories. Ointments, lotions, and eye drops may be envisaged for topical administration.

The said unit forms are dosed to allow a daily administration of from 0.01 to 20 mg of active principle per kg of body weight, according to the presentation form.

In order to prepare tablets, a pharmaceutical vehicle which may be composed of diluents such as, for example, lactose, microcrystalline cellulose, starch and formulation adjuvants, for instance binders (polyvinylpyrrolidone, hydroxypropylmethylcellulose, etc.), glidants, for instance silica, lubricants, for instance magnesium stearate, stearic acid, glyceryl tribehenate or sodium stearylfumarate is added to the micronized or non-micronized active principle. Wetting agents or surfactants such as sodium lauryl sulfate may also be added.

The preparation techniques may be direct tableting, dry granulation, wet granulation or hot melting.

The tablets may be plain, coated, for example with sucrose, or coated with various polymers or other suitable materials. They may be designed to allow a rapid, delayed or sustained release of the active principle by means of polymer matrices or specific polymers used in the coating.

In order to prepare gel capsules, the active principle is mixed with dry pharmaceutical vehicles (simple mixing, dry or wet granulation, or hot melting) or liquid or semi-solid pharmaceutical vehicles.

The gel capsules may be hard or soft, and uncoated or film-coated, so as to have rapid, sustained or delayed activity (for example for an enteric form).

A composition in the form of a syrup or elixir or for administration in the form of drops may contain the active principle together with a sweetener, preferably a calorie-free sweetener, methylparaben or propylparaben as antiseptic, a flavor enhancer and a colorant.

The water-dispersible powders and granules may contain the active principle mixed with dispersants or wetting agents, or dispersants such as polyvinylpyrrolidone, and also with sweeteners and flavor enhancers.

For rectal administration, use is made of suppositories prepared with binders that melt at the rectal temperature, for example cocoa butter or polyethylene glycols.

For parenteral administration, aqueous suspensions, isotonic saline solutions or injectable sterile solutions containing pharmacologically compatible dispersants and/or wetting agents, for example propylene glycol or butylene glycol, are used.

The active principle may also be formulated in the form of microcapsules, optionally with one or more supports or additives, or with a polymer matrix or with a cyclodextrin (transdermal patches, sustained-release forms).

The topical compositions according to the invention comprise a medium that is compatible with the skin. They may especially be in the form of aqueous, alcoholic or aqueous-alcoholic solutions, gels, water-in-oil or oil-in-water emulsions having the appearance of a cream or a gel, microemulsions or aerosols, or alternatively in the form of vesicular dispersions containing ionic and/or nonionic lipids. These presentation forms are prepared according to the usual methods of the fields under consideration.

Finally, the pharmaceutical compositions according to the invention may contain, along with a compound of general formula (I), other active principles that may be useful in the treatment of the disorders and diseases indicated above.

The invention claimed is:

1. A compound corresponding to the general formula (I)

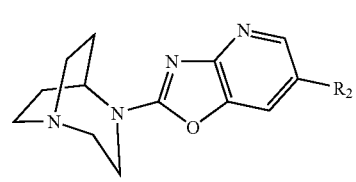

(I)

in which $R_2$ represents a 3-thienyl group, in the form of a base or of an acid-addition salt.

2. 4-(6-Thien-3-yl-oxazolo[4,5-b]pyrid-2-yl)-1,4-diazabicyclo[3.2.2]nonane in the form of a base or an acid-addition salt according to claim 1.

3. 4-(6-Thien-3-yl-oxazolo[4,5-b]pyrid-2-yl)-1,4-diazabicyclo[3.2.2]nonane hydrobromide 1:2 according to claim 2.

4. A pharmaceutical composition containing a compound as claimed in claim 1 and an excipient.

5. A pharmaceutical composition containing a compound as claimed in claim 2 and an excipient.

6. A pharmaceutical composition containing a compound as claimed in claim 3 and an excipient.

7. A method for the treatment of a disease selected from the group consisting of schizophrenia, Alzheimer's disease, Parkinson's disease, Down's syndrome, Korsakoff's alcoholic syndrome, vascular dementia, depression, anxiety, panic attack and obsessive-compulsive behavior, which comprises administering to a patient in need of such treatment an effective amount of a compound as claimed in claim 1.

8. A method for the treatment of a disease selected from the group consisting of schizophrenia, Alzheimer's disease, Parkinson's disease, Down's syndrome, Korsakoff's alcoholic syndrome, vascular dementia, depression, anxiety, panic attack and obsessive-compulsive behavior, which comprises administering to a patient in need of such treatment an effective amount of a compound as claimed in claim 2.

9. A method for the treatment of a disease selected from the group consisting of schizophrenia, Alzheimer's disease, Parkinson's disease, Down's syndrome, Korsakoff's alcoholic syndrome, vascular dementia, depression, anxiety, panic attack and obsessive-compulsive behavior, which comprises administering to a patient in need of such treatment an effective amount of a compound as claimed in claim 3.

* * * * *

UNITED STATES PATENT AND TRADEMARK OFFICE
CERTIFICATE OF CORRECTION

PATENT NO.        : 7,119,087 B2                                   Page 1 of 1
APPLICATION NO. : 10/495936
DATED             : October 10, 2006
INVENTOR(S)       : Frederic Galli et al.

It is certified that error appears in the above-identified patent and that said Letters Patent is hereby corrected as shown below:

Column 2, lines 31 and 32 read "by chromatography on a silica plate, elating with a 90/10/1 mixture of chloroform, methanol and aqueous anunonia," and should read -- by chromatography on a silica plate, eluting with a 90/10/1 mixture of chloroform, methanol and aqueous ammonia --.

Column 2, lines 42 and 43 read "4-(6-Methyloxazolo[5,4-b]pyrid-2-yl)-1,4-diazabicyclo [3.2.2]nonane hydrobromide 1:2," and should read -- 4-(6-Methyloxazolo[4,5-b]pyrid-2-yl)-1,4-diazabicyclo[3.2.2]nonane hydrobromide 1:2 --.

Column 2, line 45 reads "0.3 g (0.93 mmol) of 4-(6-bromooxazolo[5,4-b]pyrid-2-," and should read --0.3 g (0.93 mmol) of 4-(6-bromooxazolo[4,5-b]pyrid-2- --.

Column 2, line 60 reads "by addition of 024 ml of a 33% solution of hydrobromic acid," and should read -- by addition of 0.24 ml of a 33% solution of hydrobromic acid --.

Column 4, line 15 reads "GF/C# filters pretreated for 3 hours with 0.05% polyethyl-," and should read -- GF/C$^{TM}$ filters pretreated for 3 hours with 0.05% polyethyl- --.

Signed and Sealed this

Third Day of July, 2007

JON W. DUDAS
*Director of the United States Patent and Trademark Office*